(12) United States Patent
Goodchild

(10) Patent No.: US 7,357,133 B2
(45) Date of Patent: Apr. 15, 2008

(54) TRIGGERING CIRCUIT FOR AN AEROSOL DRUG-DISPENSING DEVICE

(75) Inventor: Martin Scott Goodchild, Reach (GB)

(73) Assignee: The Technology Partnership, Melbourn, Royston (GB)

( * ) Notice: Subject to any disclaimer, the term of this patent is extended or adjusted under 35 U.S.C. 154(b) by 824 days.

(21) Appl. No.: 10/416,307

(22) PCT Filed: Nov. 7, 2001

(86) PCT No.: PCT/GB01/04963

§ 371 (c)(1),
(2), (4) Date: Jul. 17, 2003

(87) PCT Pub. No.: WO02/38206

PCT Pub. Date: May 16, 2002

(65) Prior Publication Data
US 2004/0050382 A1   Mar. 18, 2004

(30) Foreign Application Priority Data
Nov. 13, 2000   (EP) ................................. 00310065

(51) Int. Cl.
*A61M 11/00* (2006.01)
*A61M 15/00* (2006.01)
*A61M 16/10* (2006.01)
*G01P 5/06* (2006.01)

(52) U.S. Cl. .......................... 128/200.14; 128/203.12; 73/861.85

(58) Field of Classification Search ........... 128/200.14, 128/200.16, 203.12, 203.15, 203.21, 203.23; 73/204.15, 204.18, 861.85
See application file for complete search history.

(56) References Cited

U.S. PATENT DOCUMENTS

| | | | |
|---|---|---|---|
| 3,352,154 A | | 11/1967 | Djorup |
| 3,991,304 A | * | 11/1976 | Hillsman ..................... 600/538 |
| 4,706,664 A | * | 11/1987 | Snook et al. .......... 128/204.23 |
| 5,487,378 A | * | 1/1996 | Robertson et al. ...... 128/200.16 |
| 5,743,252 A | | 4/1998 | Rubsamen et al. |
| 6,470,741 B1 | * | 10/2002 | Fathollahzadeh ........ 73/204.15 |

FOREIGN PATENT DOCUMENTS

GB   WO 92/07599   3/1992

\* cited by examiner

*Primary Examiner*—Danton D. DeMille
*Assistant Examiner*—Kristen C. Matter (57) ABSTRACT

An electronic gas flow triggering circuit for use in an aerosol drug dispensing device has a voltage source and a self-nulling circuit to which voltage is supplied from the voltage source. A hot wire anemometer filament forms a component of the bridge circuit which is adapted to maintain a constant resistance of the anemometer filament, the bridge drive voltage being dependent upon the gas flow across the anemometer filament. A comparator compares the bridge output voltage with a reference voltage and provides a triggering signal to operate the device if the bridge drive voltage is greater than the reference voltage.

4 Claims, 8 Drawing Sheets

TRIGGERING CIRCUIT FOR AN AEROSOL DRUG-DISPENSING DEVICE

BACKGROUND OF THE INVENTION

This invention relates to a triggering circuit for use in an aerosol drug dispensing device, and in particular, to a triggering circuit for detecting the operation of the device by a user.

Prior trigger circuits do not readily discriminate between a real triggering event, i.e. a patient inhaling on the device, and a false event, i.e. the movement of the device through the air or changes in ambient conditions. If the circuit were to be triggered by a false event, the device would be operated when the user was not ready to receive the drug and therefore that dose of the drug would be wasted. Thus, the present invention aims to provide a control circuit which overcomes the above problem.

WO92/07599 discloses a portable inhalation device for the administration of medicament in the form of aerosolised fine particles or droplets of liquid to the respiratory system of a patient. The inhalation device comprises a bridge circuit which creates an electrical output signal dependent upon the resistance in a hot wire anemometer. The resistance of this element varies as the flow across it changes and accordingly, the bridge circuit is not self nulling.

SUMMARY OF THE INVENTION

According to the present invention, there is provided an electronic gas flow triggering circuit for use in an aerosol drug dispensing device, the circuit including:

a voltage source;

a self-nulling bridge circuit to which voltage is supplied from the voltage source;

a hot wire anemometer filament forming a component of the bridge circuit which is adapted to maintain a constant resistance of the anemometer filament, the bridge drive voltage being dependent upon the gas flow across the anemometer filament; and a comparator for comparing the bridge drive voltage with a reference voltage such that a trigger signal is provided if a certain rate of change of gas flow is exceeded.

As real and false events can be distinguished based on the time frame within which they occur, the present invention compares the bridge drive voltage with a reference voltage composed of the low frequency signals contained within the bridge drive voltage. When the bridge drive voltage reaches a predetermined level relative to the reference voltage, the gas flow circuit is triggered. The present invention therefore is sensitive to rate of change of gas flow and is only triggered by the higher frequency signals that correspond to a patient inhaling on the device.

Accordingly, the present invention provides a self nulling bridge circuit in which the resistance of the hot wire anemometer is maintained at a constant value. By maintaining the resistance of the hot wire anemometer at a constant value, the sensor element can be remotely located away from the instrumentation electronics. The resistance of the sensor element is significantly larger than the resistances of the connecting wires and any electrical connectors employed. A constant sensor element resistance also eliminates errors resulting from potential divider ratio variations that would occur in a variable resistance sensor element system. When compared to the prior art, the present invention provides a simpler trigger mechanism in which there is no significant temperature change and only a single measurement is required.

Preferably, the bridge circuit is a Wheatstone bridge.

The reference voltage may be derived from the bridge drive voltage, thus preventing erroneous triggering due to changes in ambient temperature.

The reference voltage may be derived from the bridge drive voltage and may be filtered to pass only low frequency signals. Thus, the reference voltage does not change appreciably with rapid changes in air flow whereas the unfiltered bridge drive voltage signal (the measurement drive) responds quickly to rapid changes in air flow. The sensitivity of the detection circuit may be set by dividing down the measurement voltage such that the more the voltage is divided, the less sensitive the trigger becomes, and the faster a patient needs to inhale on the device in order to trigger the circuit.

Thus, the comparison of filtered and unfiltered voltage signals provide a simple and effective means of sensing the rate of change of air flow rather than just the change in the air flow so that the control system discriminates between real and false triggering events.

Air passing over the anemometer filament causes it to cool which, in turn, effects the power delivered to the filament because, as the bridge circuit is operating in a self-nulling mode, it attempts to maintain the filament temperature by means of a closed loop control system. Monitoring the voltage supply to the bridge provides a means for sensing changes in the air flow, i.e. the anemometer and the bridge form an air flow sensor.

BRIEF DESCRIPTION OF THE DRAWINGS

An embodiment of the present invention will now be described with reference to the accompanying drawings, in which.

DESCRIPTION OF THE INVENTION

As can be seen from FIGS. 1 to 6, a drug dispensing device 25 forming part of a drug delivery system has a hollow casing 1 in which a reservoir body 2 is slidably mounted. A spray head mounting assembly 3 is attached to one end of the casing 1, the mounting assembly 3 comprising spray head assembly 3a, clamping means 4, diaphragm clamp 11a and seal 17. A main return spring 5 is provided in a recess 29 in the casing 1 between a lower face 2a of the reservoir body 2 and a notch 29a in diaphragm ring 30 to support the reservoir body 2, biassed towards its topmost position (as shown), within the casing 1. The reservoir body 2 is movable between a first and second position within the casing 1.

Figure 1:
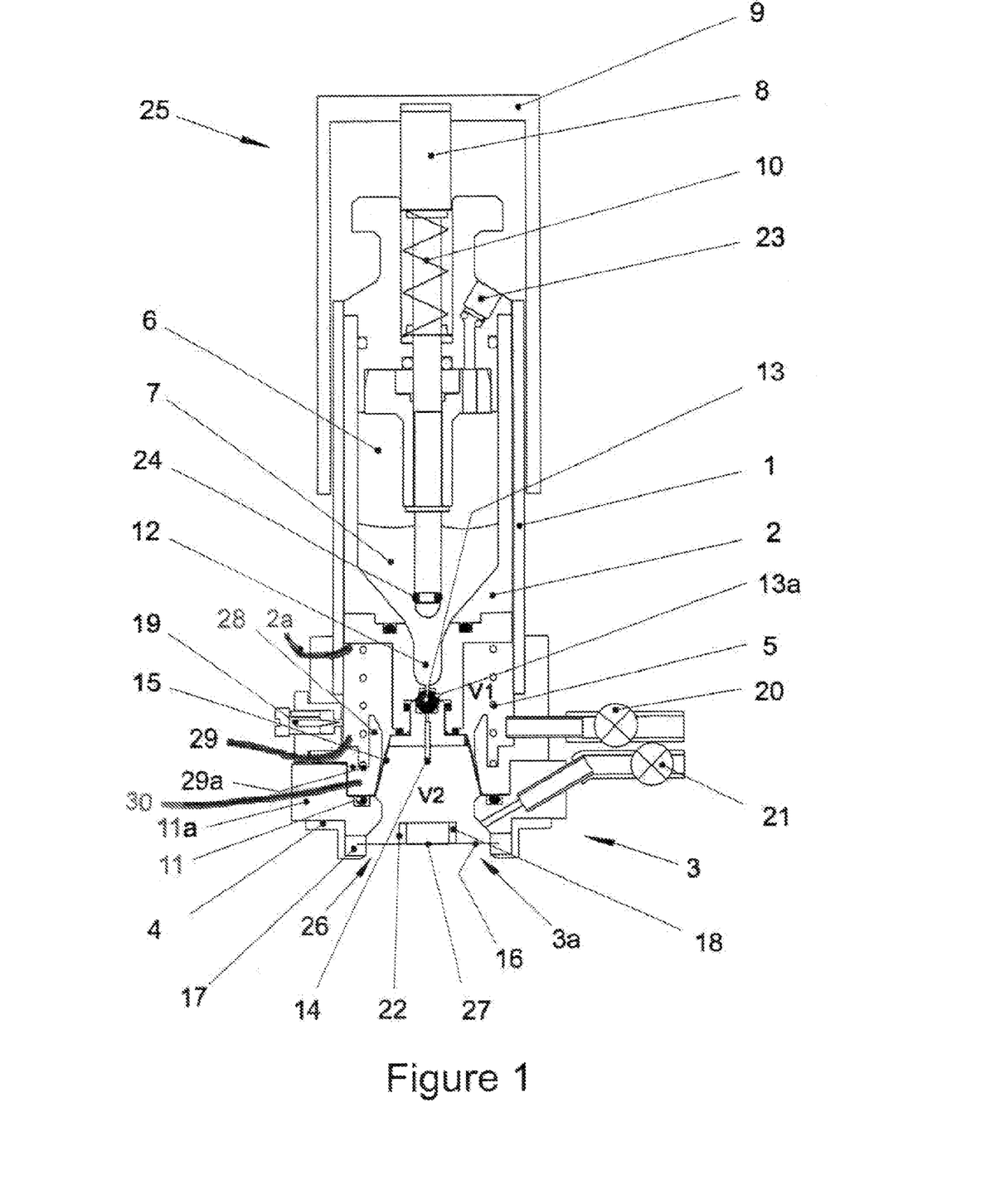
FIG. 1 shows a cross sectional side view of a device for dispensing a pharmacologically active liquid.

The reservoir body 2 has a reservoir cavity 6 in which a liquid drug 7 is stored and which can be topped-up via a re-fill port 23. A plunger 8 is provided within the reservoir body 2 and extends out of the upper (as shown in the figures) end of the reservoir body 2, such that it engages with a cap 9 which covers the top of the device 25. A plunger return spring 10 is provided which extends from the reservoir body 2 and biases the plunger 8 out of the reservoir cavity 6.

A metering cavity 12 is provided at the lower end of the reservoir cavity 6 and the metering cavity 12 is in liquid communication, via a one-way ball valve 13, with a dispensing conduit or tube 14 provided within the lower end of the reservoir body 2. An elastomeric diaphragm 15 is provided around the lower portion of the reservoir body 2 and is joined at its outer edge to the casing 1 by diaphragm clamp 11a and a seal 11, which is an O-ring, to define, together with the reservoir body 2 and the casing 1, a chamber V1.

The spray head mounting assembly 3 is provided with an outlet 26 covered by a membrane 16 which, together with the lower portion of the reservoir body 2, the spray head mounting assembly 3 and the elastomeric diaphragm 15, defines a chamber V2. The membrane 16 is retained by a seal 17 and is provided with a perforate portion 27 overwhich a holding reservoir 18 is provided and which can receive liquid drug 7 through the dispensing conduit or tube 14 in use. The perforate portion 27 of the membrane 16 has perforations 50 (see FIGS. 8a and 8b) of a reverse taper and this is described in greater detail with reference to FIGS. 8a and 8b.

The spray head mounting assembly 3 is provided with a damping inlet valve 19 leading into the chamber V1, a first one-way exhaust valve 20 from the chamber V1 and a second one-way exhaust valve 21 from the chamber V2.

FIG. 1 shows the device 25 at rest prior to metering a predefined dose of drug 7 into the holding reservoir 18. In this state, both the main return spring 5 and the plunger return spring 10 are extended so that the reservoir body 2 and the plunger 8 have been pushed fully upwards against physical stops (not shown).

The elastomeric diaphragm 15 is stretched from its normally flat state and acts as a flexible wall, separating the two chambers V1 and V2. These chambers are initially at ambient pressure and the perforations 50 in the perforate portion 27 of membrane 16 are dry and open.

The operation of the device shown in FIG. 1 will now be described with reference to FIGS. 2 to 6.

Figure 2:
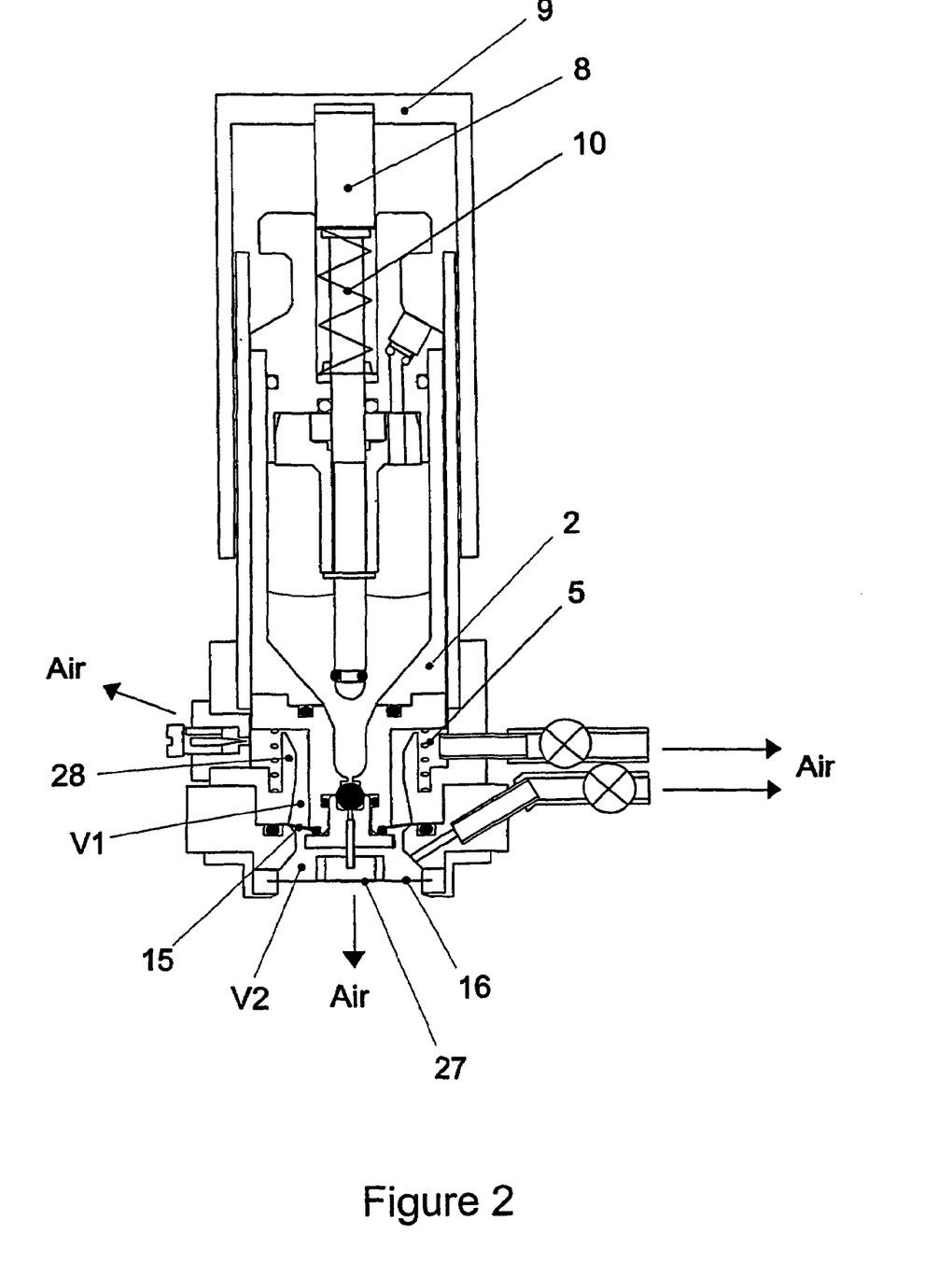
FIGS. 2 to 6 show successive stages during operation of the device of FIG. 1.

To initiate operation of the device 25, the cap 9 is pressed downwards 9a (see FIG. 2). The reservoir body 2 and the plunger 8 are moved downwards at approximately the same rate, compressing the main return spring 5 until the reservoir body 2 reaches physical stops 28. At this stage the force exerted on the plunger return spring 10 is less than its preload. The lower end of the dispensing conduit or tube 14 is now positioned close to the inner surface of the membrane 16.

The reservoir body 2 forms an air-tight sliding seal with the casing 1. Therefore, as the reservoir body 2 descends, air is displaced from the chamber V1, through the first one-way exhaust valve 20 and the elastomeric diaphragm 15 returns towards its relaxed, almost flat state. At the same time, air is displaced from the chamber V2 through the second one-way exhaust valve 21, through the damping valve 19, and through the perforate portion 27 of the membrane 16.

Figure 3:
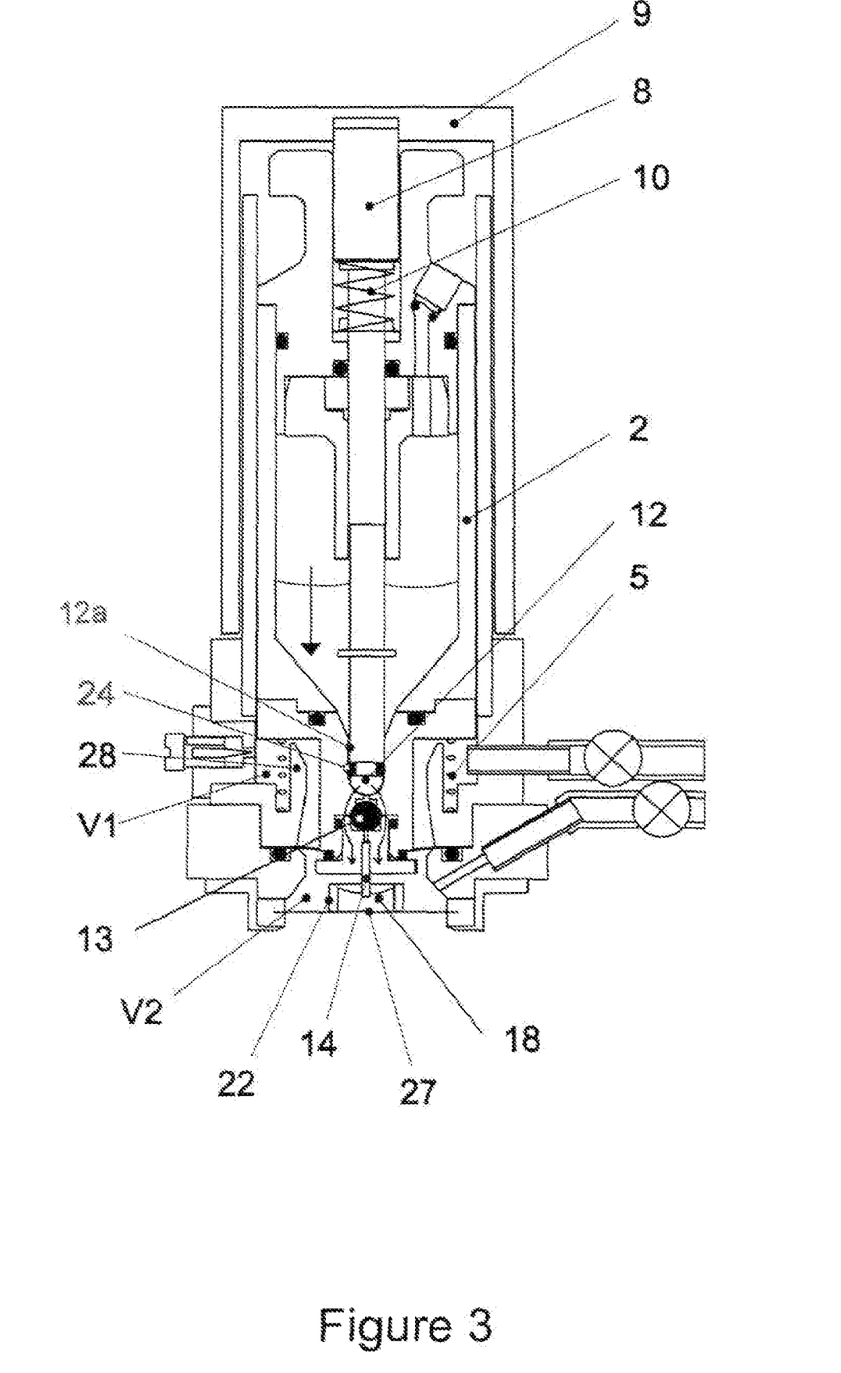

As can be seen in FIG. 3, once the reservoir body 2 has reached its physical stops 28, further depression of the cap 9 compresses the plunger return spring 10. This pushes the plunger 8 into the metering cavity 12 (see FIG. 1). The plunger 8 is provided with a plunger seal 24 which engages with the side wall 12a of the metering cavity 12 to form a seal therewith. This traps a metered dose of the liquid drug 7 in the metering cavity 12. The sealing pressure of the plunger seal 24 against the side-wall 12a of the metering cavity 12 is greater than the sealing pressure of the elastomeric ball valve 13 against the ball valve seat 13a. Therefore, as the plunger 8 is depressed further, the trapped dose of liquid drug 7 is displaced from the metering cavity 12 past 13b the one-way elastomeric ball valve 13, through the dispensing conduit or tube 14 and into the holding reservoir 18. The holding reservoir 18 has a side-wall 22 which is either coated with or formed of PTFE. In this configuration, all of the perforations 50 in the perforate portion 27 of membrane 16 are now covered with liquid drug 7a.

Figure 4:
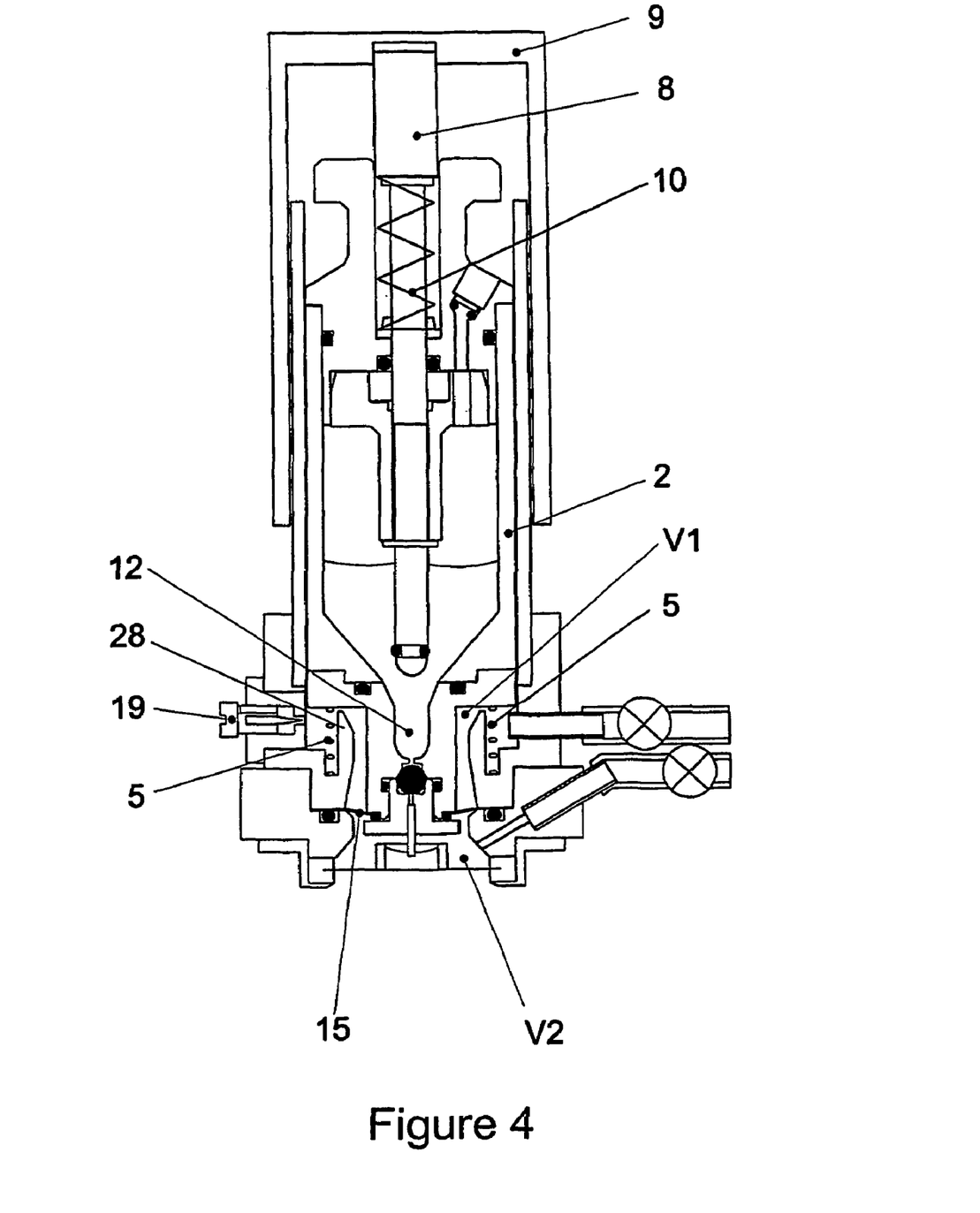
Figure 5:
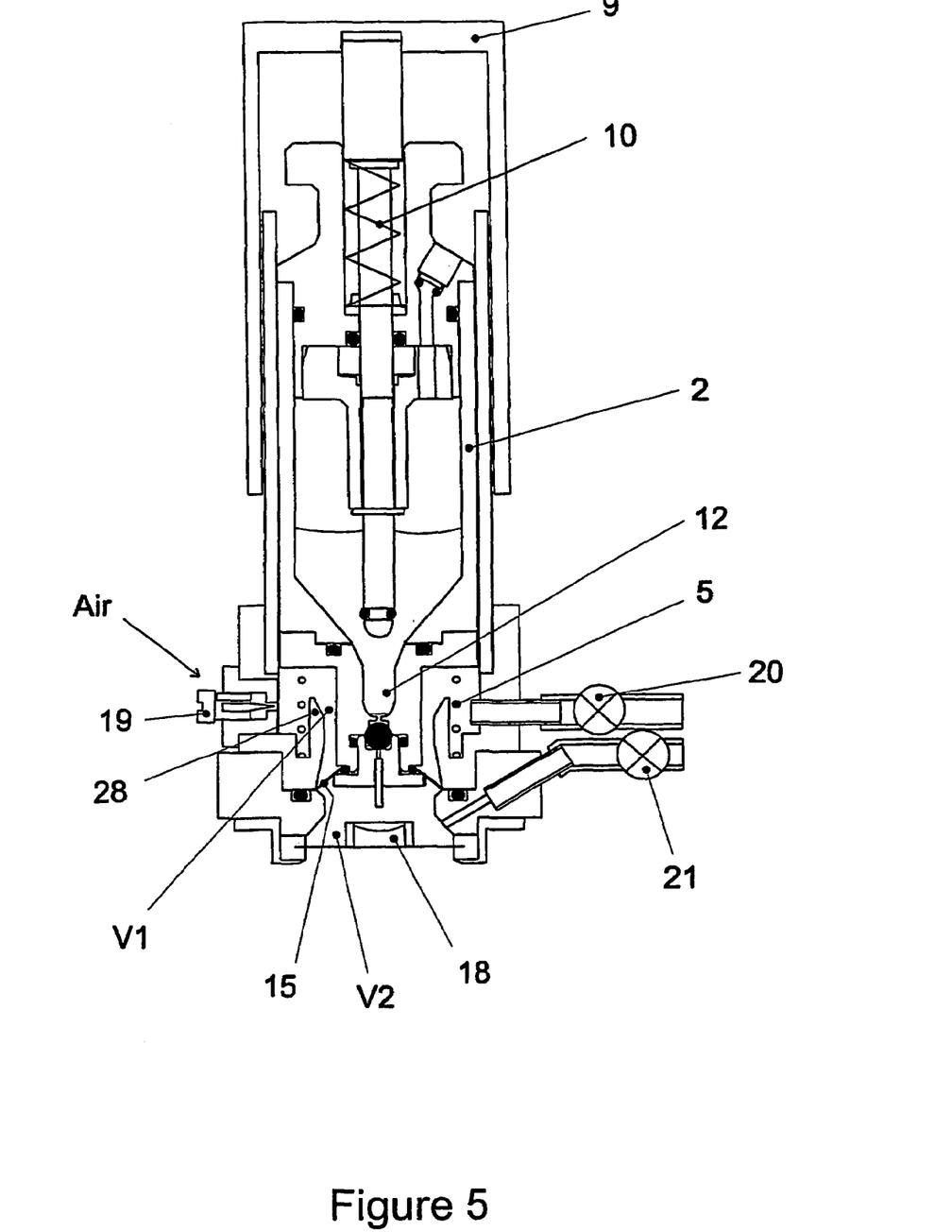

Once the cap 9 is released, as shown in FIG. 4, the plunger return spring 10 starts to expand, pushing the plunger 8 out of the metering cavity 12, thus creating a partial vacuum in the metering cavity 12. The elastomeric ball valve 13 remains closed. The plunger return spring 10 is strong enough to overcome this partial vacuum so as to push the plunger 8 clear of the metering cavity 12 until it reaches a physical stop (not shown). This partial vacuum pressure reduces as the plunger 8 is withdrawn from the metering cavity 12 until the pressure drop across the plunger seal 24 exceeds the sealing pressure against the side-wall 12a of the metering cavity 12. A small amount of liquid drug 7 can then flow past the plunger seal 24 into the metering cavity 12 as the plunger 8 is withdrawn. The main return spring 5 is able to extend, pushing 2a the reservoir body 2 upwards as shown in FIG. 5. This then causes the chambers V1 and V2 to expand and the elastomeric diaphragm 15 to stretch.

Air cannot enter through the one-way valves 20, 21 or through the perforate portion 27 of membrane 16 as the perforations 50 are now covered by liquid drug 7a. The perforations 50 resist air ingress because of the surface tension of the liquid drug forming menisci across the perforations 50 in the perforate portion 27 and therefore, as the chambers V1 and V2 expand, the pressures within those chambers decrease below ambient pressure. The reservoir body 2 continues to move upwards 2a until the restoring force of the main return spring 5 is stalled by the opposing forces created, in the main, by the negative pressures in the chambers V1 and V2 and by the tension in the elastomeric diaphragm 15.

When the damping valve 19 is fully closed, no air can enter the chamber V1 and so the main return spring 5 will not extend far before it is stalled by the negative pressures generated in the chambers V1, V2 and by tension in the elastomeric diaphragm 15.

However, when the damping valve 19 is slightly open, it will allow air to enter into, and conversely exhaust from, the chamber V1 at a rate determined by the restoring force of the main return spring 5. Therefore, as the main return spring 5 pushes the reservoir body 2 upwards 2a, the volume of chamber V1 expands at a controlled rate until the reservoir body 2 reaches a predefined physical stop (not shown) (see FIG. 6).

Figure 6:
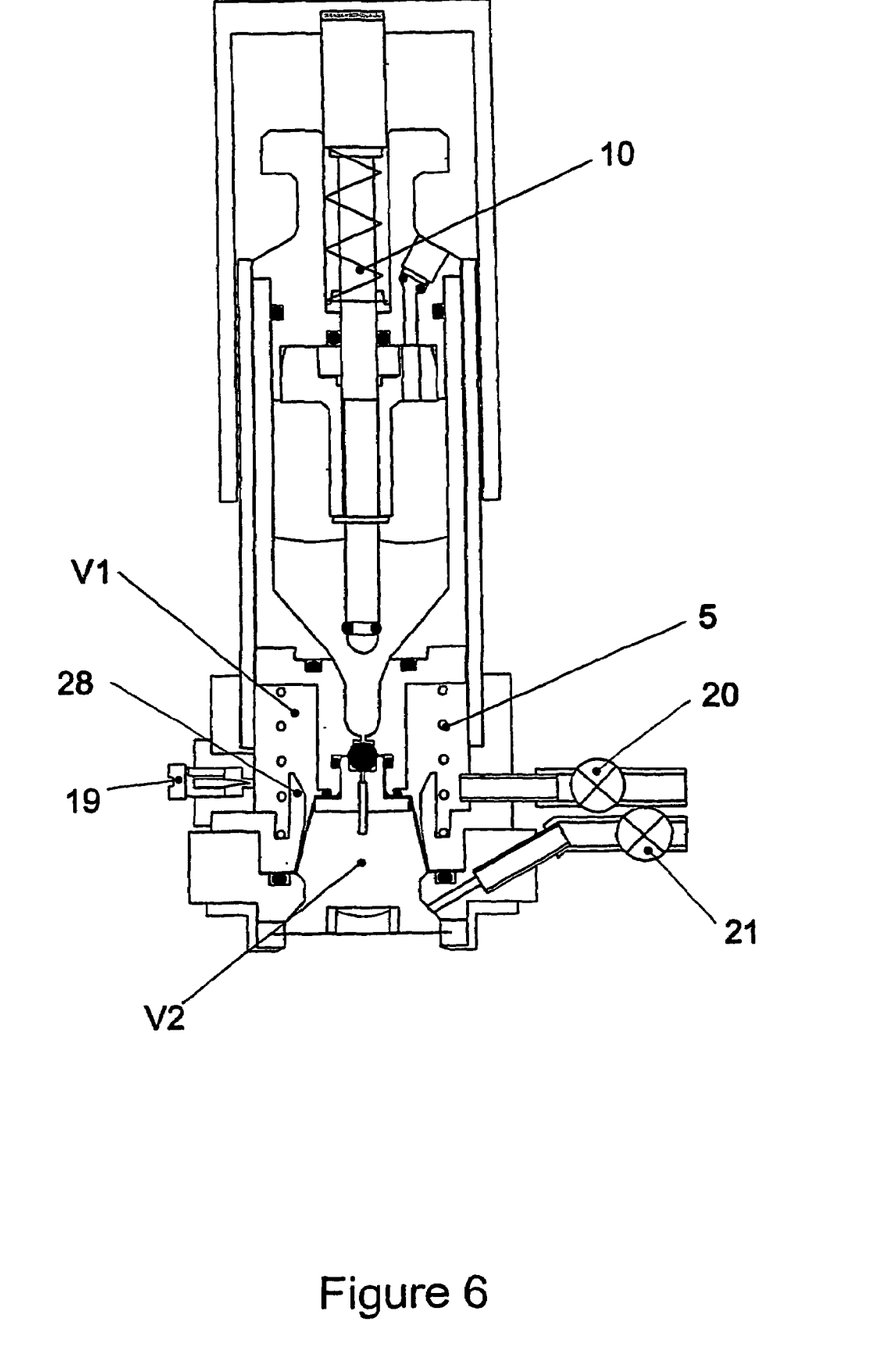

The main return spring 5 also causes the elastomeric diaphragm 15 to stretch at a controlled rate which, in turn, causes the volume of the chamber V2 to expand at a controlled rate. The pressure within the chamber V2 behind the spray head assembly 3a therefore reduces at a controlled rate.

The physical stop (not shown) for the upward movement of the reservoir body 2 limits the extension of the stretched elastomeric diaphragm 15 and defines the final volume change of the chamber V2 and thus the target negative pressure achieved in V2. At this stage, the pressure in the chamber V1 is at ambient pressure.

Therefore, the net result is that the target (operating) negative pressure, which is close to the bubble point pressure for the spray head assembly 3*a* (the bubble point pressure being the pressure differential at which air bubbles enter the chamber V2 through the perforations 50 in the perforate portion 27, by overcoming the surface tension of the menisci of liquid drug), can be reached at a controlled rate without air being ingested through the membrane 16.

If the negative pressure in the chamber V2 is generated too quickly, i.e. by opening the damping valve 19 too far, then the surface tension of the liquid drug covering the perforations in the perforate portion 27 of the membrane 16 will be overcome. Air will then be ingested rapidly through the perforate portion 27, hence cancelling the negative pressure in the chamber V2. In the absence of a negative pressure, the drug dispensing device 25 will not generate a spray.

It should be noted that the rate of air admission and exhaustion through damping, valve 19 is much less than the rate of exhaustion through the first one way exhaust valve 20.

Figure 7:
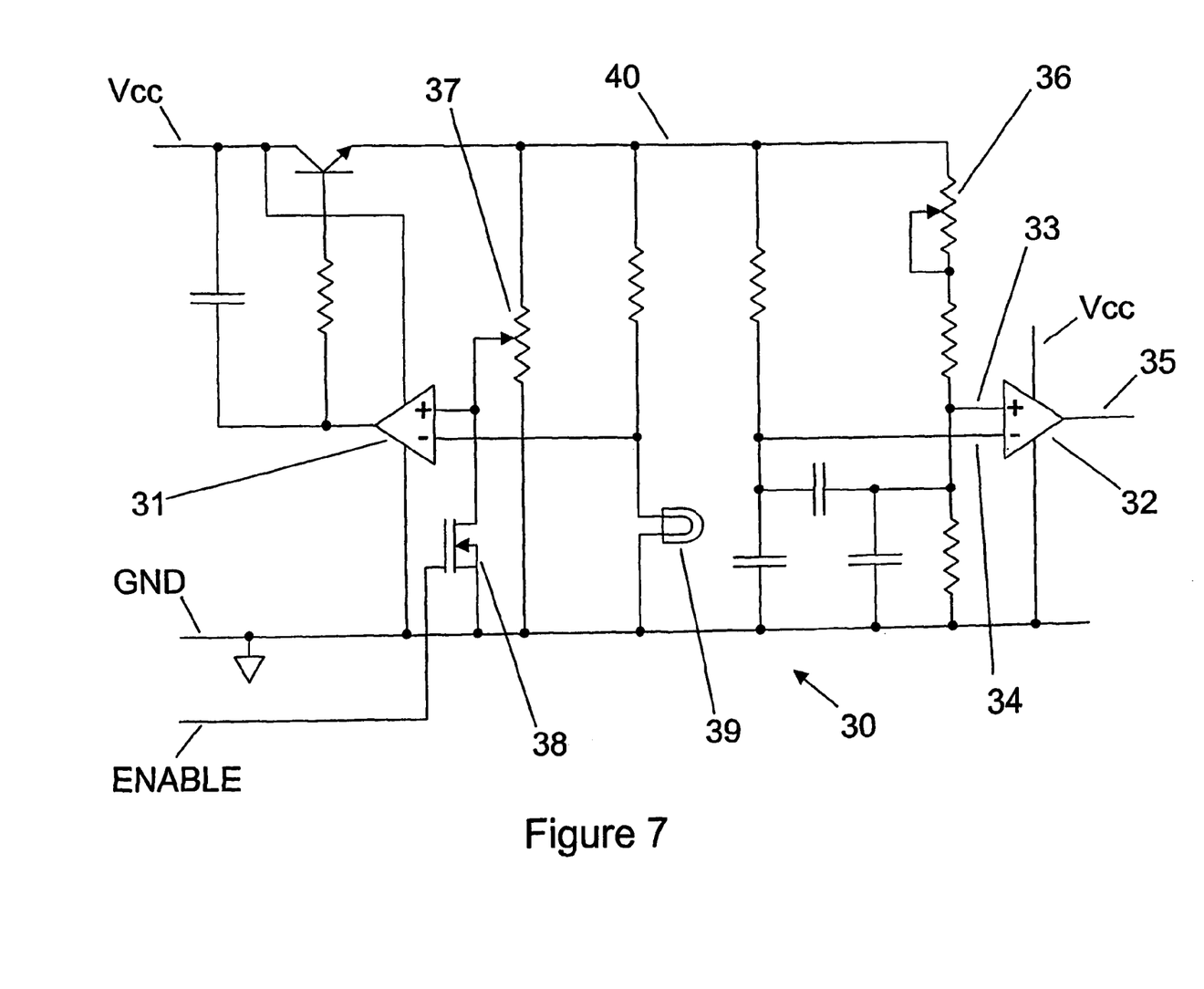
FIG. 7 shows a trigger circuit for controlling the dispensing of the pharmacologically active liquid.

An electronic control circuit 30 as shown in FIG. 7 triggers the delivery of the liquid drug through the perforate portion 27 of the membrane 16 by controlling membrane actuating means (not shown) such as piezoelectrically activated vibrating means. The control system uses a small hot wire anemometer 39 to monitor air flow into the drug delivery system. The anemometer 39 senses when a patient is inhaling and trying to trigger the spray head delivery.

Figure 8A:
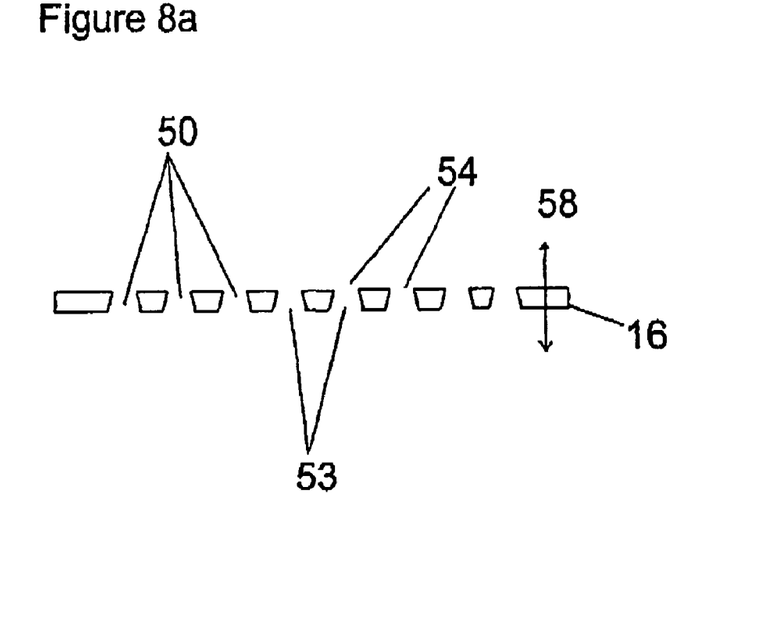
FIGS. 8a and 8b illustrate, in section, preferred forms of the perforate membrane for the device of FIG. 1.

The maximum spring load of the plunger return spring 10 preferably should not exceed 20N. This therefore limits the force that a user must exert in order to operate the device.

The plunger return spring 10 is preloaded and this preload should be greater than the fully compressed load in the main return spring 5. This ensures that the reservoir body 2 is fully down against its physical stop 28 before the dose is metered into the holding reservoir 18. If the dose is metered from the dispensing aperture 14 when the reservoir body 2 is not fully down, all or part of the dose may miss the holding reservoir 18. The target negative pressure in the chamber V2 will then not be reached when the cap 9 is released because the perforations in the perforate portion 27 of the membrane 16 will remain dry and open.

As the plunger 8 is withdrawn from the reservoir cavity 12 a partial vacuum is created between the closed one-way elastomeric ball-valve 13 and the plunger seal 24. The spring force range of the plunger return spring 10 must be sufficient to lift the plunger 8 out of the reservoir cavity 12 when the cap 9 when the cap is released, in order to create a pressure difference across the plunger seal 24 (between the liquid drug 7 in reservoir cavity 6 and the elastomeric ball valve 13) which exceeds the sealing pressure of the plunger seal 24 against the side-wall 12*a* of the reservoir cavity 12. Liquid drug 7 is then above to flow past the plunger seal 24 and into the reservoir cavity 12 as the plunger 8 is withdrawn. This has the advantage of minimising foam generation within the reservoir cavity 12 especially with liquid drugs containing surfactants as part of their formulation.

The spring force range of the main return spring 5 must be sufficient to lift the reservoir body 2 against the negative pressures generated within the chambers V1, V2, the stretching of the elastomeric diaphragm 15 and the friction of the sliding seal between the reservoir body 2 and the casing 1.

The maximum tension in the elastomeric diaphragm 15, which is achieved when the reservoir body 2 is at rest, must be high enough to maintain the target negative pressure within the chamber V2 without the elastomeric diaphragm 15 deforming under that negative pressure. This tensional force must not be high enough to prevent the main return spring 5 from lifting the reservoir body 2 up against the predetermined physical stop during the generation of the negative pressures.

In summary, the extension force of the plunger return spring 10 is greater than the extension force of the main return spring 5 which is greater than the tensional force of the elastomeric diaphragm 15.

From FIG. 7, it can be seen that the control circuit employs two operational amplifiers (op-amps) 31, 32, which can supply output voltages over the full power supply range, i.e. between the supply voltage Vcc and ground GND. Op-amp 31 is in closed loop configuration with a Wheatstone bridge to maintain a constant resistance of the anemometer filament 39. The drive voltage 40 for the Wheatstone bridge is supplied to the op-amp 32 which is configured as a voltage comparator. The comparator is a switching device having a measurement input and a reference input. When the measurement voltage 33 is higher than the reference voltage 34, the output 35 from the op-amp 32 switches from GND to Vcc.

Circuits of this type are well known in anemometry. However the circuit of FIG. 7 shows a simple implementation of a circuit which can discriminate between high and low rates of change of air flow. The RC time constant used for the reference voltage 34 is set so that it can respond, in a damped manner, to slowly varying conditions such as changes in ambient conditions and to the normal slow breathing of a patient. Therefore, the reference voltage 34 is insensitive to fast rates of change in air flow during the patient inhalation cycle. The measurement voltage 33 at the comparator op-amp 32 is an attenuated signal from the Wheatstone bridge drive voltage 40, but does not have a long time constant filter and so reacts directly with the patient's inhalation.

If the patient inhales at a sufficiently high volume rate, then the measurement voltage 33 will exceed the reference voltage 34 due to the difference in the time constant of the reference and measurement voltages. In order for this to happen, a certain threshold of rate of change of air flow must be exceeded. When the measurement voltage 33 exceeds the reference voltage input 34, there will be a change in the voltage state at the output 35. Since the comparator circuit does not have any feedback, it is operating in a high gain mode and so has only two output states, 0 v and Vcc. Thus, it is possible to couple this circuit directly to TTL logic devices.

Two variable resistors 36, 37 are provided within the control circuit 30. The variable resistor 36 in the comparator is used to adjust the level of attenuation applied to the measurement voltage 33, which sets the sensitivity of the circuit to the rate of change of patient's inhalation. The second variable resistor 37, in the Wheatstone bridge, is provided to set the temperature of the anemometer filament 39 and is used to set the minimum rate of change of air flow that the circuit can detect. Thus, these adjustments allow a high degree of flexibility in the installation of the anemometer as a breath trigger device.

A field effect transistor 38 is used to alter the reference ratio of the Wheatstone bridge thus enabling or disabling the air flow sensor via "ENABLE". In this way, the power consumption of the control circuit 30 is reduced, allowing the device to have a useful operating life when powered by batteries.

FIG. 8*a* shows cross-sectional detail of a first example perforate membrane 16, which is operable to vibrate substantially in the direction of arrow 58 and which is suitable for use with the drug dispensing device 25 to produce fine aerosol sprays. In one embodiment, the membrane 16 comprises a circular layer of polymer which contains a plurality of tapered conical perforations 50. Each perforation 50 has openings 53 in the front exit face and openings 54 in the rear entry face, which perforations are laid out in a square lattice. Such perforations may be introduced into polymer membranes by, for example, laser-drilling with an excimer laser.

Figure 8B:
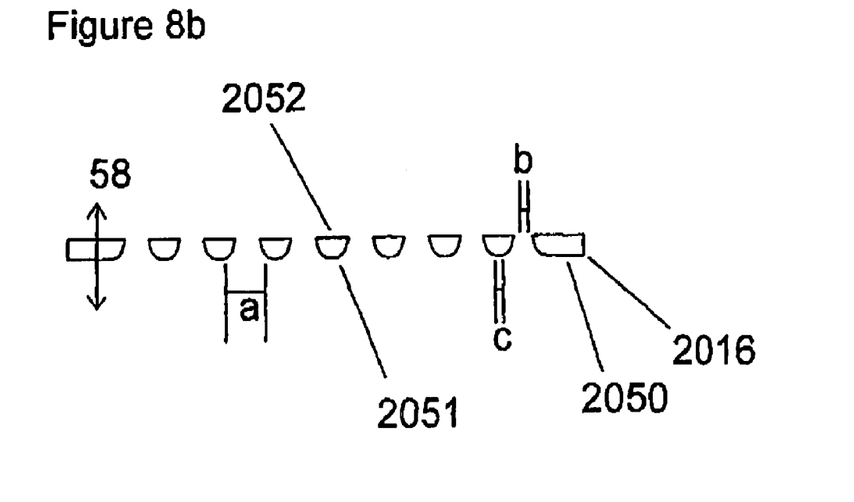

FIG. 8b shows cross-sectional detail of a second example perforate membrane 2016, which membrane is operable to vibrate substantially and suitable for use with drug dispensing device 25 in the direction of arrow 58. The membrane is formed as a circular disc of diameter 8 mm from electro-formed nickel, and is manufactured, for example, by Stork Veco of Eerbeek, The Netherlands. Its thickness is 70 microns and is formed with a plurality of perforations shown at 2050 which, at 'front' face 2051, are of diameter shown at "a" of 120 microns and at 'rear' face 2052 are of diameter shown at "b" of 30 microns. The perforations are laid out in an equilateral triangular lattice of pitch 170 μm. The profile of the perforations varies smoothly between the front and rear face diameters through the membrane thickness with substantially flat 'land' regions (shown at "c") of smallest dimension 50 μm in front face 2051.

The invention claimed is:

1. An electronic gas flow triggering circuit for use in an aerosol drug dispensing device, the circuit including:

a voltage source;

a self-nulling bridge circuit to which voltage is supplied from the voltage source;

a hot wire anemometer filament forming a component of the bridge circuit which is adapted to maintain a constant resistance of the anemometer filament, the bridge drive voltage being dependent upon the gas flow across the anemometer filament; and a comparator for comparing the bridge drive voltage with a reference voltage such that a trigger signal is provided if a certain rate of change of gas flow is exceeded.

2. A triggering circuit according to claim 1, wherein the bridge circuit is a Wheatstone bridge.

3. A triggering circuit according to claim 1, wherein the reference voltage is derived from the bridge drive voltage, to prevent erroneous triggering due to changes in ambient temperature.

4. A triggering circuit according to claim 3, wherein the reference voltage is filtered to pass only low frequency signals. It is requested that multiple dependencies be removed from the application. If any multiple dependencies remain after amendment, said multiple dependencies should be deleted and the claim made dependent on the next previous claim.

* * * * *